US011116952B2

(12) United States Patent
Ogbu

(10) Patent No.: US 11,116,952 B2
(45) Date of Patent: *Sep. 14, 2021

(54) STEAM THERAPY EQUIPMENT FOR GOOD HEALTH AND WELLNESS

(71) Applicant: Basil C. Ogbu, Detroit, MI (US)

(72) Inventor: Basil C. Ogbu, Detroit, MI (US)

( * ) Notice: Subject to any disclaimer, the term of this patent is extended or adjusted under 35 U.S.C. 154(b) by 447 days.

This patent is subject to a terminal disclaimer.

(21) Appl. No.: 16/118,085

(22) Filed: Aug. 30, 2018

(65) Prior Publication Data

US 2018/0369551 A1 Dec. 27, 2018

Related U.S. Application Data

(63) Continuation of application No. 15/625,471, filed on Jun. 16, 2017, now Pat. No. 10,086,182, which is a
(Continued)

(51) Int. Cl.
*A61M 37/00* (2006.01)
*A61K 36/58* (2006.01)
(Continued)

(52) U.S. Cl.
CPC ........... *A61M 37/00* (2013.01); *A61F 7/0053* (2013.01); *A61F 7/0085* (2013.01); *A61H 33/06* (2013.01); *A61H 33/065* (2013.01); *A61H 33/066* (2013.01); *A61H 33/12* (2013.01); *A61H 33/6068* (2013.01); *A61H 35/02* (2013.01); *A61K 36/18* (2013.01); *A61K 36/185* (2013.01); *A61K 36/21* (2013.01); *A61K 36/22* (2013.01); *A61K 36/23* (2013.01); *A61K 36/28* (2013.01); *A61K 36/31* (2013.01); *A61K 36/45* (2013.01); *A61K 36/47* (2013.01); *A61K 36/484* (2013.01); *A61K 36/52* (2013.01); *A61K 36/54* (2013.01); *A61K 36/58* (2013.01); *A61K 36/61* (2013.01); *A61K 36/73* (2013.01); *A61K 36/736* (2013.01); *A61K 36/752* (2013.01); *A61K 36/889* (2013.01); *A61K 36/9066* (2013.01); *A61M 37/0015* (2013.01); *F24F 6/02* (2013.01); *F24F 6/18* (2013.01); *A61F 2007/0055* (2013.01); *A61F 2007/0062* (2013.01); *A61F 2007/0086* (2013.01); *A61F 2007/0087* (2013.01); *A61F 2007/0261* (2013.01); *A61H 2033/068* (2013.01); *A61H 2201/0207* (2013.01); *A61H 2201/0257* (2013.01); *A61H 2201/10* (2013.01); *A61H 2201/5043* (2013.01);
(Continued)

(58) Field of Classification Search
CPC .. A61K 2300/00; A61K 36/185; A61K 36/21; A61K 36/22; A61K 36/23; A61K 36/28; A61K 36/31; A61K 36/45; A61K 36/47; A61K 36/484; A61K 36/52; A61K 36/54; A61K 36/58; A61K 36/61; A61K 36/73; A61K 36/736; A61K 36/752; A61K 36/889; A61K 36/9066; A61K 36/18; A61F 2007/0055; A61F 2007/0062; A61F 2007/0086; A61F 2007/0087; A61F 2007/0261; A61F 7/0053; A61F 7/0085; A61H 2033/068; A61H 2201/0207; A61H 2201/0257; A61H 2201/5043; A61H 2201/5048; A61H 2201/5058; A61H 2201/5071; A61H 2201/5082; A61H 2201/10; A61H 2205/024; A61H 2205/08; A61H 33/06; A61H 33/065; A61H 33/066; A61H 33/12; A61H 33/6068; A61H 35/02; A61M 2205/3368; A61M 2205/36; A61M 37/00; A61M 37/0015; F24F 6/18; F24F 6/02; Y02A 50/30
See application file for complete search history.

(56) References Cited

U.S. PATENT DOCUMENTS

| | | | |
|---|---|---|---|
| 1,797,554 | A | 3/1931 | Obidine |
| 2,076,171 | A | 4/1937 | Besuzzi |

(Continued)

FOREIGN PATENT DOCUMENTS

| | | |
|---|---|---|
| FR | 2730633 | 2/1995 |
| KR | 20090077636 A | 7/2009 |

OTHER PUBLICATIONS

SaunaFin "Aromatherapy for Saunas: What Essential Oil is Best for You" Oct. 25, 2017, retrieved from <URL:saunafin.com/blog/home-saunas/aromatherapy-sauna-essential-oil/> on Dec. 31, 2020, 2 pages (Year: 2017).*

(Continued)

*Primary Examiner* — Aaron J Kosar
(74) *Attorney, Agent, or Firm* — Dykema Gossett PLLC

(57) ABSTRACT

A steam therapy equipment including a vessel for heating a mixture of water and organic materials, a compressor to inject pressurized air into the vessel producing pressurized steam. The pressurized steam is conducted into the equipment via one or more valves. The therapy equipment is formed from at least one panel and may include a supporting frame. The therapy equipment includes a temperature sensor to measure the temperature inside the therapy equipment when pressurized steam is admitted via the valves. A patient enters the equipment and is exposed to the pressurized steam, causing dilation of the skin pores of the patient, whereby toxins are removed from the patient. One or more applicators may conduct pressurized steam to specific portions of the body of the patient. The patient may be provided with a portion of the mixture to consume as part of the steam therapy treatment.

20 Claims, 6 Drawing Sheets

Related U.S. Application Data continuation-in-part of application No. 15/178,519, filed on Jun. 9, 2016, now abandoned.

(51) Int. Cl.

| | |
|---|---|
| *A61K 36/61* | (2006.01) |
| *A61K 36/18* | (2006.01) |
| *A61K 36/52* | (2006.01) |
| *A61K 36/31* | (2006.01) |
| *A61K 36/54* | (2006.01) |
| *A61K 36/9066* | (2006.01) |
| *A61K 36/484* | (2006.01) |
| *A61K 36/752* | (2006.01) |
| *A61K 36/736* | (2006.01) |
| *A61K 36/28* | (2006.01) |
| *A61K 36/23* | (2006.01) |
| *A61K 36/21* | (2006.01) |
| *A61K 36/889* | (2006.01) |
| *A61K 36/45* | (2006.01) |
| *A61K 36/185* | (2006.01) |
| *A61K 36/73* | (2006.01) |
| *A61K 36/22* | (2006.01) |
| *A61H 33/06* | (2006.01) |
| *A61H 35/02* | (2006.01) |
| *A61H 33/12* | (2006.01) |
| *A61H 33/00* | (2006.01) |
| *A61K 36/47* | (2006.01) |
| *F24F 6/18* | (2006.01) |
| *A61F 7/00* | (2006.01) |
| *F24F 6/02* | (2006.01) |
| *A61F 7/02* | (2006.01) |

(52) U.S. Cl.
CPC ............ *A61H 2201/5048* (2013.01); *A61H 2201/5058* (2013.01); *A61H 2201/5071* (2013.01); *A61H 2201/5082* (2013.01); *A61H 2205/024* (2013.01); *A61H 2205/08* (2013.01); *A61M 2205/3368* (2013.01); *A61M 2205/36* (2013.01)

(56) References Cited

U.S. PATENT DOCUMENTS

| | | |
|---|---|---|
| 3,351,737 A | 11/1967 | Katzman et al. |
| 4,044,772 A | 8/1977 | Schloss |
| 4,432,103 A | 2/1984 | Hunziker |
| 6,623,511 B1 * | 9/2003 | Daffer .................. A61F 7/0053 128/898 |
| 6,745,412 B1 | 6/2004 | Egeresi |
| 8,021,702 B2 | 9/2011 | Brady |
| 10,086,182 B2 * | 10/2018 | Ogbu .................. A61K 36/889 |
| 2007/0000043 A1 | 1/2007 | Nakayama |
| 2007/0018344 A1 | 1/2007 | Mueller et al. |
| 2007/0147808 A1 | 6/2007 | Egeresi |
| 2009/0044311 A1 | 2/2009 | Lipponen |
| 2013/0067656 A1 | 3/2013 | Brunner et al. |
| 2014/0364777 A1 | 12/2014 | Swyer |

OTHER PUBLICATIONS

Pramod Kerkar, MD, Wonders of Steam Inhalation of Benefits of Inhaling Steam, epainassist.com, May 31, 2017, https://www.epainassist.com/articles/wonders-of-steam-inhalation, 7 pages.

* cited by examiner

STEAM THERAPY EQUIPMENT FOR GOOD HEALTH AND WELLNESS

CROSS-REFERENCE TO RELATED APPLICATIONS

This application is a continuation of U.S. application Ser. No. 15/625,471 (the '471 application), filed 16 Jun. 2017, now pending, which is a continuation-in-part of U.S. application Ser. No. 15/178,519, filed 9 Jun. 2016, now abandoned (the '519 application). The '519 application and the '471 application are both hereby incorporated by reference as though fully set forth herein.

THE NAMES OF THE PARTIES TO A JOINT RESEARCH AGREEMENT

Basil Ogbu, Detroit, Mich. (US); John Ude, Farmington Hills, Mich. (US); Godwin Maduko, Pittsfield Twp; MI (US); Obioma Ogbu, Enugu, Nigeria (West Africa); John Brown, Basildon (United Kingdom); Jideofor Ogbu, Enugu, Nigeria (West Africa); Christian Anidi, Enugu, Nigeria (West Africa).

BACKGROUND a. Technical Field

This invention relates to naturopathic steam therapy delivery equipment; a device that delivers organic/plant compounds dissolved in steam, via the pores in the human body, to aid detoxification through enhanced perspiration/sweating, for improving health and wellness.

b. Background Art

This background description is set forth below for the purpose of providing context only. Therefore, any aspects of this background description, to the extent that it does not otherwise qualify as prior art, is neither expressly nor impliedly admitted as prior art against the instant disclosure.

The process of steam therapy as disclosed herein originated from the ancient African tribe known as the "Igbo" (the descendants of the kingdom of Judah in the Seth Region of West Africa), and is called "Ogwu Okpukpu" in the Igbo language.

In the ancient process, a person being treated (i.e., a patient), was made to sit on a small log of wood, with the person's legs astride (i.e., with a leg on either side of), the log. A small pot containing a boiled plant concoction was then placed in between the patient's legs, adjacent to the small log. A blanket was then draped over the patient, covering the patient completely, while the patient was made to lean forward, over the small pot. The patient would then be exposed to the steam emanating from the small pot and trapped beneath the blanket.

However, this ancient process has several drawbacks. The ancient process does not fully dilate the patient's skin pores nor does it deliver a sufficient amount of steam containing the organic compounds (i.e., the boiled plant concoction), to the patient's body. As a result, the ancient process has limited detoxifying effect.

What is needed then is a steam therapy equipment, or apparatus, that is capable of fully dilating a patient's skin pores to induce measured and controllable perspiration, and can also deliver sufficient amount of steam containing organic compounds to the patient's body, thereby flushing (via perspiration) the patient's body of toxins. The steam therapy equipment also includes at least one special mechanism, or an apparatus, for applying enhanced and/or limited steam (and heat) delivery to a desired, targeted portion of the patient's body.

The foregoing discussion is intended only to illustrate the present field and should not be taken as a disavowal of claim scope.

SUMMARY

In an embodiment, a method for applying steam to the human body may include placing at least one organic plant compound in a vessel (e.g., pot, container) adding water to the vessel, mixing the at least one organic plant compound with the water, heating the at least one organic compound and the water to produce steam, forcing air into the vessel via a compressor to pressurize the steam, piping the pressurized steam into a steam therapy equipment, wherein the therapy equipment comprises equipment including at least one wall, an access door, a temperature control system, a communication system, at least one shutoff valve, a fluid drain, placing a patient within the therapy equipment, and exposing the patient to the pressurized steam.

In an embodiment, a method for applying steam to the human body may include heating the air within the equipment via the pressurized steam and increasing the humidity of the air within the equipment via the pressurized steam.

In an embodiment, a method for applying steam to the human body may include causing the pores of the skin of the patient to dilate via the pressurized steam and causing the pressurized steam to be absorbed into the skin and/or bloodstream of the patient.

In an embodiment, a method for applying steam to the human body may include inducing perspiration in the patient and detoxifying the patient via the perspiration.

In an embodiment, a method for applying steam to the human body may include attaching a steam applicator to the steam therapy equipment via a flexible adapter to reduce and/or receive the pressurized steam, placing the steam applicator in contact with a portion of the body of the patient, and concentrating the pressurized steam on the portion of the body via the steam applicator for a predetermined period of time.

In an embodiment, a method for applying steam to the human body may include removing the patient from the therapy equipment for a predetermined period. The flexible adapter is attached to the steam applicator, and the applicator is strapped on the patient to receive the pressurized steam via the steam therapy equipment for a predetermined period of time.

In an embodiment, a method for applying steam to the human body may include providing the patient with the mixture of the at least one organic plant compound and the water to be consumed by the patient.

In an embodiment, a method for applying steam to the human body may include an organic plant compound including a combination selected from: a) neem leaves; b) pawpaw leaves; c) guava leaves; d) orange leaves; e) soursop leaves, and f) black walnut bark.

In an embodiment, a method for applying steam to the human body may include an organic plant compound including a combination selected from: a) horse radish leaves; b) avocado leaves; c) cherry leaves; d) guava leaves; and e) turmeric root.

In an embodiment, a method for applying steam to the human body may include an organic plant compound including a combination selected from: a) licorice root; b) lemon peel; c) almond leaves; d) chicory; e) carrot; f) spinach leaves; g) coconut; h) bilberry; and i) Indian gooseberry.

In an embodiment, a method for applying steam to the human body may include an organic plant compound including a combination selected from: a) apple leaves; b) mango leaves; c) beet root; d) spinach leaves; and e) carrot.

In an embodiment, a system for applying steam to the human body may include a steam generator, a compressor in fluid communication with the steam generator, a therapy equipment in fluid communication via at least one valve with the steam generator and the compressor.

In an embodiment, a system for applying steam to the human body may include at least one wall, wherein the at least one wall is supported by a frame, a door, a temperature control system, a communications system, and a drain.

In an embodiment, a system for applying steam to the human body may include at least one steam applicator in fluid communication with the steam generator and the compressor via a flexible adapter.

In an embodiment, a system for applying steam to the human body may include at least one steam applicator that includes one or more contours to sealingly engage at least a portion of the outer surface of a human body.

In an embodiment, a system for applying steam to the human body may include at least one steam applicator that includes a plurality of vent holes.

In an embodiment, a method for applying steam to the human body may include placing at least one organic plant compound in a vessel, adding water to the vessel, mixing the at least one organic plant compound with the water, heating the at least one organic compound and the water to produce steam, forcing air into the vessel via a compressor to pressurize the steam, piping the pressurized steam into a steam therapy equipment, wherein the therapy equipment comprises at least one steam applicator, and exposing the patient to the pressurized steam via the at least one steam applicator.

In an embodiment, a method for applying steam to the human body may include attaching a steam applicator to the steam therapy equipment via a flexible adapter to reduce the pressurized steam, placing the steam applicator in contact with a portion of the body of the patient, and concentrating the pressurized steam on the portion of the body via the steam applicator for a predetermined period of time.

In an embodiment, a method for applying steam to the human body may include providing the patient with the mixture of the at least one organic plant compound and the water to be consumed by the patient.

In an embodiment, a method for applying steam to the human body may include sealingly engaging the at least one steam applicator against at least a portion of the outer surface of a human body.

The foregoing and other aspects, features, details, utilities, and advantages of the present disclosure will be apparent from reading the following description and claims, and from reviewing the accompanying drawings.

DETAILED DESCRIPTION

Figure 1:
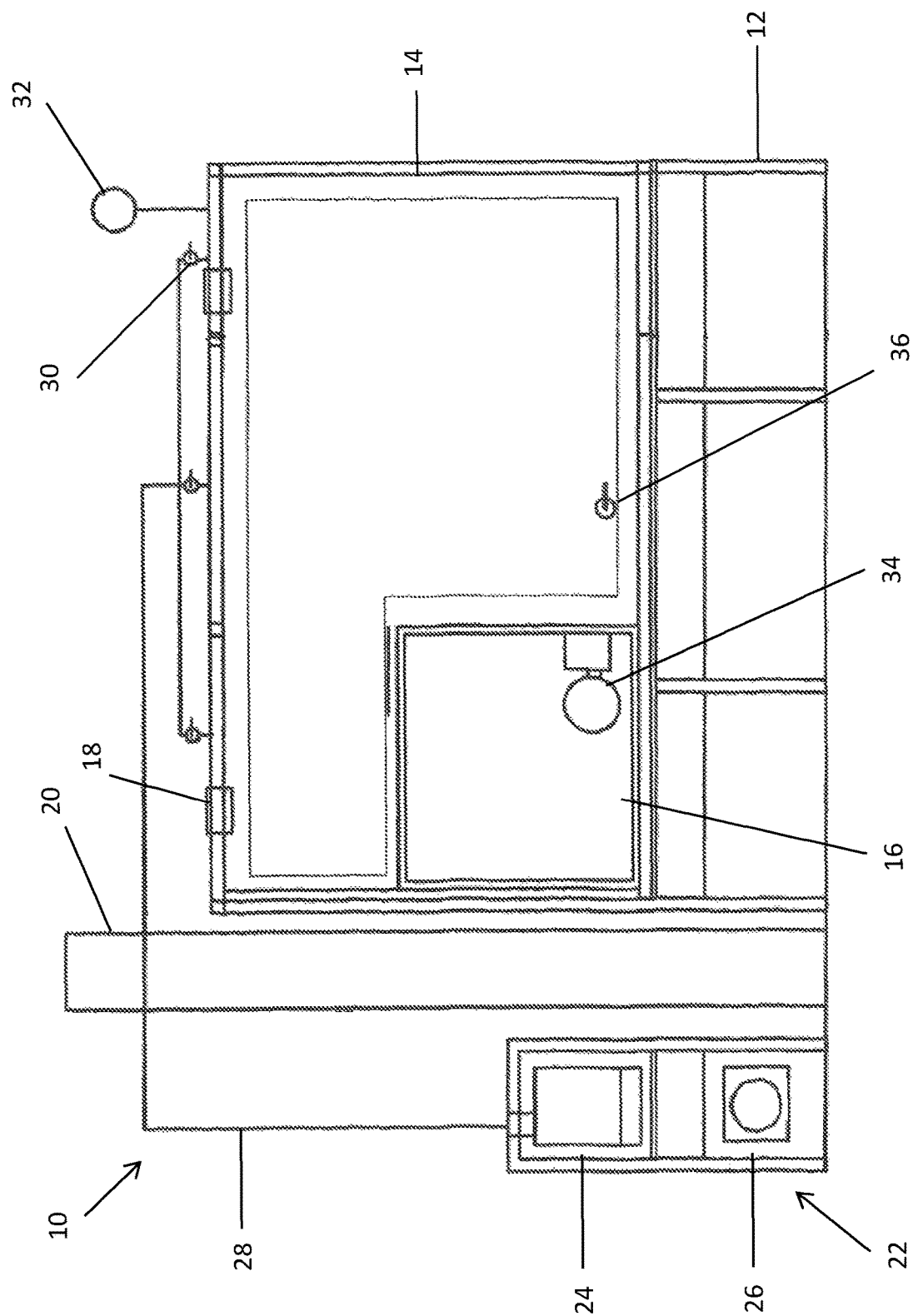
FIG. 1 is a front view generally illustrating an embodiment of a steam therapy equipment, in accordance with teachings of the present disclosure.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

Before proceeding to a detailed description of a steam therapy equipment, an overview description of such an apparatus will first be described. The initial description will describe in general how a patient interacts with the apparatus, in both setup and in executing the steam therapy treatment in order to obtain detoxification and other health benefits. This document will also describe various embodiments for implementing the apparatus, as well as variations.

Referring now to the drawings wherein like reference numerals are used to identify identical or similar components in the various views, FIGS. 1, 2, 3A-3B, 4, and 5 are diagrammatic views of a therapy equipment system/apparatus 10 in an exemplary environment. As described in the Background, a perimeter frame 12 supports one or more panels 14 to enclose a space. Frame 12 may be constructed of materials such as steel, aluminum, or wood formed in a tubular shape, though other shapes are also to be considered (e.g. box, square, flat). Frame 12 may be configured into a plurality of individual elements that may join to one or more other elements of frame 12. Frame 12 may include attachments means for securing one or more panels 14 to frame 12, such as, but not limited to, bolts, rivets, and/or screws. Panel 14 may be constructed of one or more layers, including but not limited to, insulating layers. Panel 14 may be configured such that one or more insulating layers are located between an outer layer and an inner layer of panel 14. For example and without limitation, the outer layer and/or inner layer of panel 14 may be constructed of aluminum, stainless steel, and/or wood, or a combination thereof. Panel 14 may include attachment points that may engage frame 12, such as threaded holes, tabs, or other mechanical fastening and/or joining means. At least one panel 14 may include a window 16, which may be configured to allow a patient within the therapy equipment 10 to see out and/or a technician/operator to see the patient within the therapy equipment 10. Window 16 may be constructed of glass and/or a plastic material (e.g., polycarbonate). Window 16 may be securely installed within panel 14 via a gasket and/or mounting frame.

In embodiments, hinges 18 may be configured to permit one panel 14 to rotate about another panel 14. For example and without limitation, one or more hinges 18 may be configured at the top of therapy equipment 10, to permit a panel 14 to rotate upward, allowing a patient 34 access to the interior of therapy equipment 10. It should be understood that one or more hinges 18 may be configured on one or more panels 14 to permit access to the interior of therapy equipment 10. For example, hinges 18 may be configured on one or more sides to enable access to one or more sides of therapy equipment 10. Panels 14 that include hinges 18 may also include sealing devices (e.g., gaskets), to prevent steam and/or water from exiting therapy equipment 10.

In embodiments, a wall 20 may be positioned between therapy equipment 10 and steam generator 22. Wall 20 may be configured to isolate therapy equipment 10 from the noise and/or heat produced by steam generator 22. Wall 20 may include one or more passages through which steam pipe 28 may pass. In embodiments, therapy equipment 10 may be in close proximity to wall 20. In embodiments, wall 20 may be in contact with therapy equipment 10 such that wall 20 may provide a degree of structural support to therapy equipment 10.

In embodiments, steam generator 22 may include a pot 24 and a compressor 26. Pot 24 may be configured to receive water and/or organic plant materials (e.g., leaves and/or bark). Pot 24 may include a heat source such that pot 24 may heat water and organic plant materials. Pot 24 may be controlled by a separate control system or be connected to the temperature control system 32 of therapy equipment 10. Pot 24 may include a fluid connection (e.g., pipe, tube), to compressor 26. Compressor 26 may be configured to pressurize air and provide the pressurized air to the pot 24 via the fluid connection. As the water and organic plant material mixture is heated in pot 24, the addition of the pressurized air from compressor 26 results in pressurized steam. The pressurized steam is utilized by therapy equipment 10.

In embodiments, pressurized steam from steam generator 22 may be conducted via piping 28 to one or more valves 30 disposed on therapy equipment 10. In embodiments, piping 28 may extend through one or more walls 20 that may be configured to isolate steam generator 22 from therapy equipment 10. In embodiments, piping 28 may include a manifold that may distribute pressurized steam about the surfaces of therapy equipment 10. For example, a manifold may be positioned on the top (e.g., roof) of therapy equipment 10 that receives pressurized steam from the steam generator 22. A plurality of piping 22 may extend from the manifold to various locations on therapy equipment 10. For example and without limitation, a plurality of piping 22 may extend to various locations on the top of therapy equipment 10. A valve 30 may be configured with each section of piping that is connected to (e.g., passes through) the interior of therapy equipment 10. In this configuration, pressurized steam may be directed into the equipment from a plurality of locations, or one location. In embodiments, a flexible adapter 56 may be connected to piping 28 and/or may be configured to receive (e.g., be connected to), one or more steam applicators 44, 46, and 48, which will be discussed in further detail below (and shown in FIGS. 6A-6C).

In embodiments, therapy equipment 10 may include a temperature sensor 32. Temperature sensor 32 may be connected to (e.g., installed on), therapy equipment 10, such as on one or more panels 14 (e.g., top, side). In embodiments, temperature sensor 32 may include additional sensors and/or devices (e.g., pressure sensor, humidity sensor, timing device).

In embodiments, patient 34 may enter a therapy equipment 10 via first panel 14 connected to a second panel 14 via hinges 18. For example, as illustrated in FIG. 1, front panel 14, including window 16, is attached to the top panel 14 via hinges 18. In order to access the interior of therapy equipment 10, a handle 36 (e.g., lever, latch), may be operated (e.g., turned), enabling patient 34 and/or a technician/attendant to open therapy equipment 10 and gain access to the interior. Patient 34 may recline (e.g., lay down), inside therapy equipment 10 on bottom panel 14. Bottom panel 14 may include comfort features (e.g., padding), that patient 34 may lay upon.

In embodiments, therapy equipment 10 may include one or more handles 36. Handles 36 may be configured to permit a panel 14 of therapy equipment to selectively open against one or more additional panels 14 via hinges 18. For example, as illustrated in FIG. 1, handle 36 is positioned at the edge of the front panel 14 of therapy equipment 10. In that position, handle 36 may operate against the bottom (i.e., floor), panel 14 of therapy equipment 10. In embodiments, handle 36 may be configured to permit a technician or operator to lift front panel 14, providing an opening to the interior to therapy equipment 10. Hinges 18 permit front panel 14 rotate upward, in this embodiment. In embodiments, handle 36 may include a latching mechanism to securely close front panel 14 against other panels 14 (e.g., bottom, top, left and right side), of therapy equipment 10 (e.g., bottom, top, left and right side).

Figure 5:
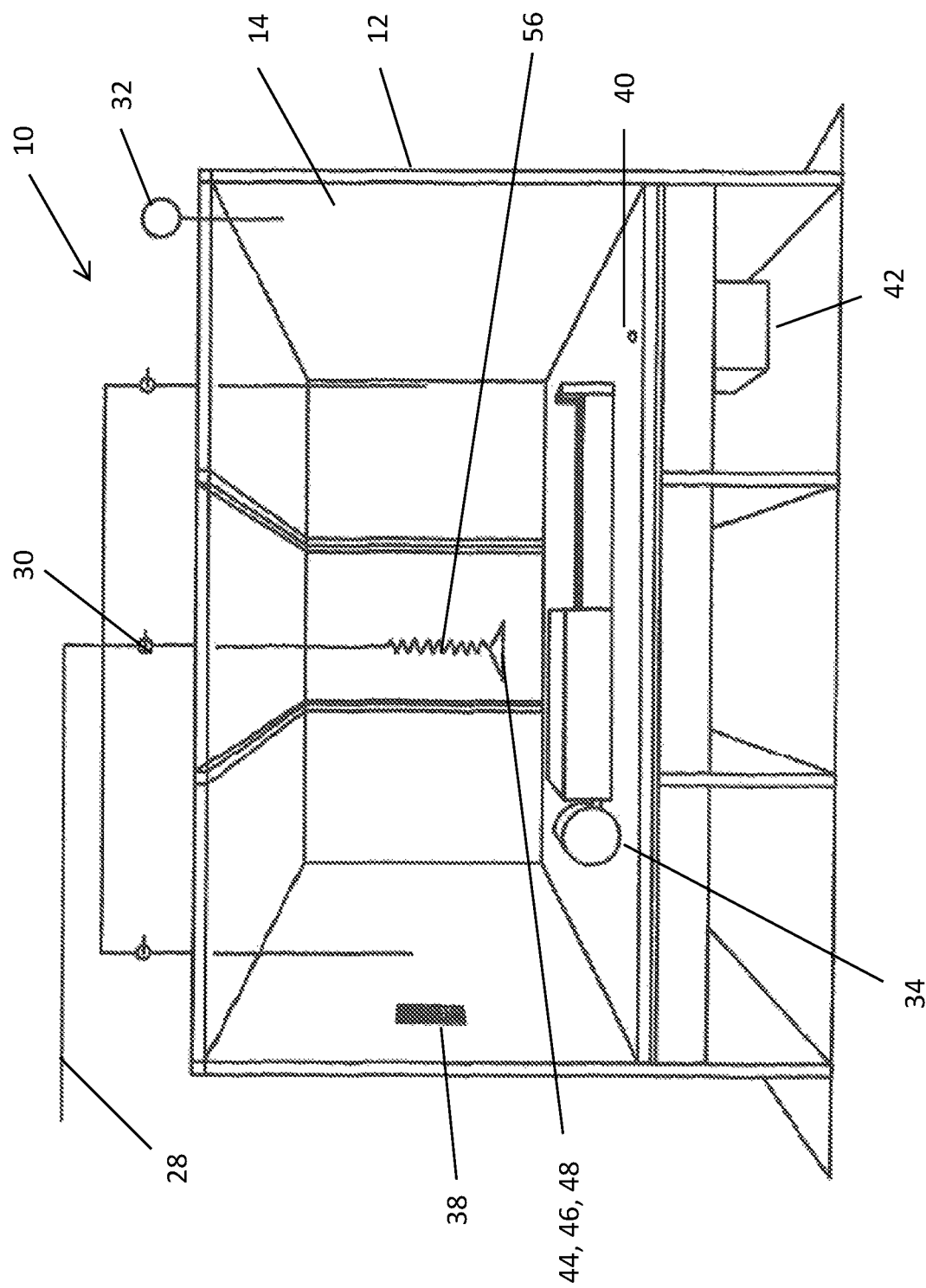
FIG. 5 is a sectional view generally illustrating an embodiment of a steam therapy equipment, in accordance with teachings of the present disclosure.

In embodiments, a therapy equipment 10 may include a communication device 38. Communication device 38 may be disposed within therapy equipment 10 (as shown in FIG. 5). Communication device 38 permits a patient 34 within therapy equipment 10 to communicate with a technician or an operator (i.e., an attendant), outside of therapy equipment 10, such as during a treatment session. Communication device 38 may include a microphone, a speaker, a video camera, and/or a video display to permit patient 34 to communicate with the other person outside of therapy equipment 10. For example, patient 34 may choose to communicate with the other person regarding the temperature inside therapy equipment 10 (e.g., too hot inside).

In embodiments, a therapy equipment 10 may include a drain 40. Drain 40 may be configured on a bottom (i.e., floor), panel 14. Bottom panel 14 may be configured with a slope (i.e., angle), such that water and/or condensation may be directed toward drain 40. Drain 40 may be located, for example, in a corner of bottom panel 14, as shown in FIG. 5. In embodiments, drain 40 may be located in the center of bottom panel 14. It should be understood that drain 40 may be positioned in a number of locations within therapy equipment 10 to permit water and/or condensation to leave the interior of therapy equipment 10.

In embodiments, a therapy equipment 10 may include a reservoir 42. Reservoir 42 may be in fluid communication with a drain 40. In embodiments, reservoir 42 may be located (e.g., mounted to), a panel 14 of therapy equipment 10. For example, as shown in FIG. 5, reservoir 42 is mounted beneath bottom panel 14 and in fluid communication with drain 40, such that water and/or condensation present in therapy equipment 10 may exit therapy equipment 10 via drain 40 and be collected in reservoir 42. In embodiments, reservoir 42 may be detachable (i.e., removable), from therapy equipment to permit a technician or an operator (i.e., an attendant), to empty reservoir 42. In embodiments, reservoir 42 may include a conduit (not shown) that may be in fluid communication with a drainage system (e.g., floor drain).

Figure 6A:
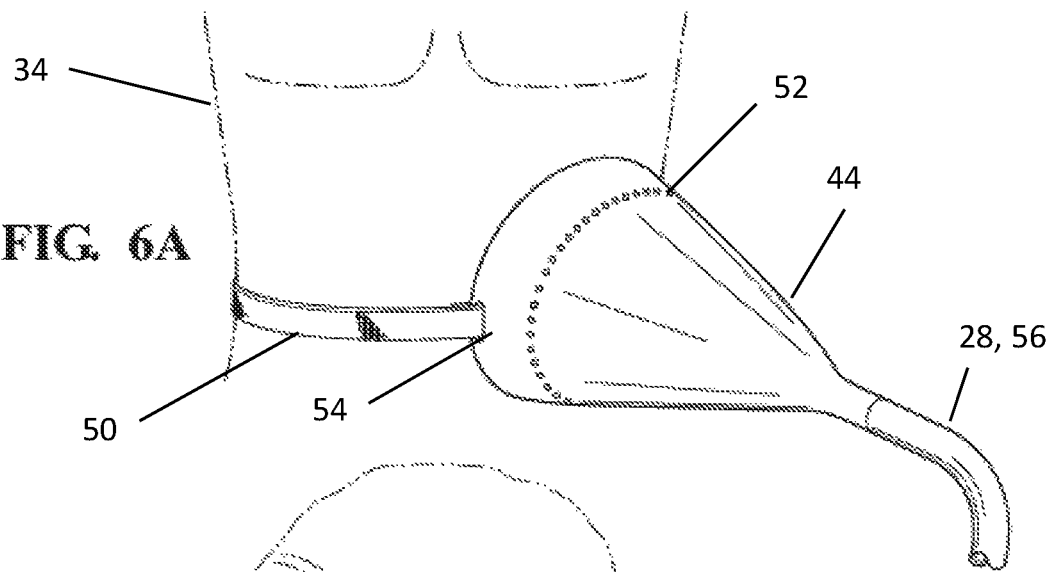
FIG. 6A is a perspective view generally illustrating an embodiment of a steam funnel applicator associated with a steam therapy equipment, in accordance with teachings of the present disclosure.

Referring now to FIG. 6A, a funnel steam applicator 44 for use with a therapy equipment 10 is shown. In embodiments, funnel steam applicator 44 may be placed in contact with a patient 34 via a strap 50. Strap 50 may be attached to engage funnel steam applicator 44, such as though slots 54. In order to concentrate pressurized steam from therapy equipment 10, an attendant or technician may secure funnel steam applicator 44 to a portion of the body of patient 34 (here, the torso of patient 34) via the strap 50. Funnel steam applicator 44 may be in fluid communication with therapy equipment 10, such that pressurized steam from steam generator 22, via therapy equipment 10, may be conducted through flexible adapter 56 (as also shown in FIG. 5), to funnel steam applicator and in contact with the torso of patient 34. In embodiments, funnel steam applicator 44 may include a plurality of vent holes 52 that are configured to allow for pressurized steam to escape and have a regulating effect on the pressurized steam applied to the torso of patient 34. In embodiments, patient 34 may be exposed to pressurized steam via the funnel steam applicator 44 in temperature ranging from 90115 F (32-46 C).

Figure 6B:
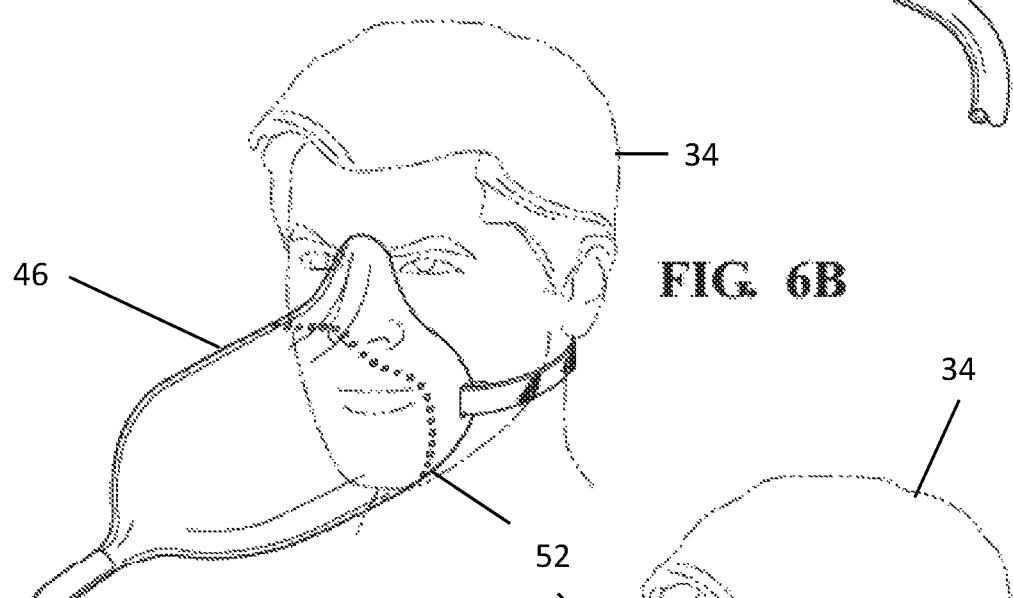
FIG. 6B is a perspective view generally illustrating an embodiment of a steam mask applicator associated with a steam therapy equipment, in accordance with teachings of the present disclosure.

Referring now to FIG. 6B, a mask steam applicator 46 for use with a therapy equipment 10 is shown. In embodiments, mask steam applicator 46 may be placed in contact with a patient 34 via a strap 50. Strap 50 may be attached to engage mask steam applicator 46, such as though slots 54. In order to concentrate pressurized steam from therapy equipment 10, an attendant or technician may secure mask steam applicator 46 to a portion of the body of patient 34 (here, the face of patient 34), via the strap 50. Mask steam applicator 46 may be in fluid communication with therapy equipment 10, such that pressurized steam from steam generator 22, via therapy equipment 10, may be conducted through piping 28 and/or flexible adapter 56 (as also shown in FIG. 5), to mask steam applicator and in contact with the face of patient 34. In embodiments, mask steam applicator 46 may include a plurality of vent holes 52 that are configured to allow for pressurized steam to escape and have a regulating effect on the pressurized steam applied to the face of patient 34. In embodiments, patient 34 may be exposed to pressurized steam via the mask steam applicator 46 in temperature ranging from 90-115 F (3246 C).

Figure 6C:
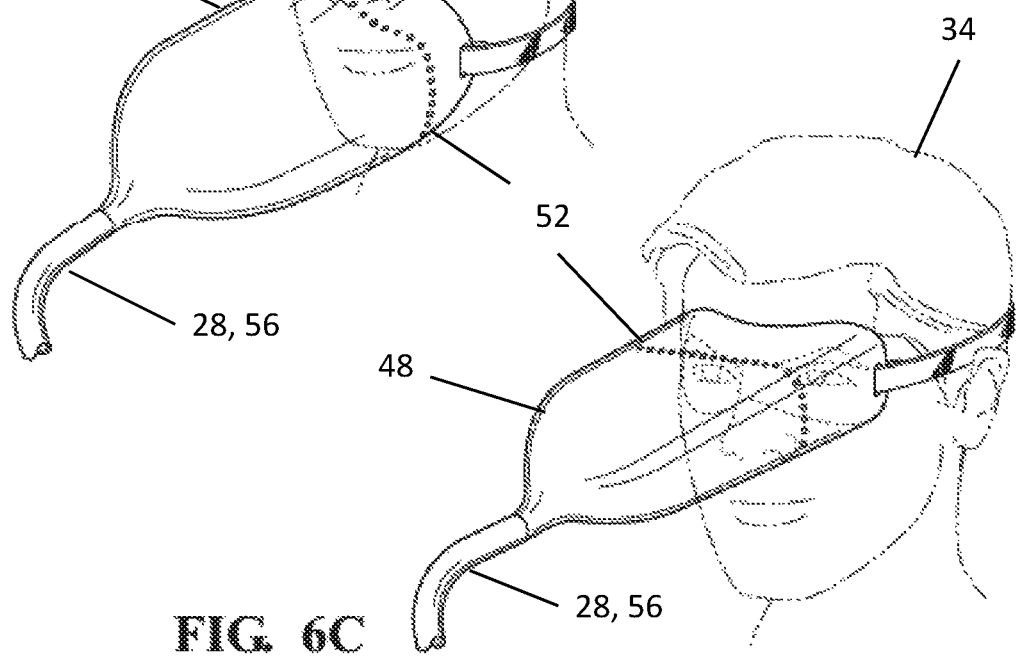
FIG. 6C is a perspective view generally illustrating an embodiment of a steam goggle applicator associated with a steam therapy equipment, in accordance with teachings of the present disclosure.

Referring now to FIG. 6C, a goggle steam applicator 48 for use with a therapy equipment 10 is shown. In embodiments, mask steam applicator 48 may be placed in contact with a patient 34 via a strap 50. Strap 50 may be attached to engage goggle steam applicator 48, such as though slots 54. In order to concentrate pressurized steam from therapy equipment 10, an attendant or technician may secure mask steam applicator 48 to a portion of the body of patient 34 (here, the eyes of patient 34), via the strap 50. Goggle steam applicator 48 may be in fluid communication with therapy equipment 10, such that pressurized steam from steam generator 22, via therapy equipment 10, may be conducted through piping 28 and/or flexible adapter 56 (as also shown in FIG. 5), to goggle steam applicator and in contact with the face of patient 34. In embodiments, goggle steam applicator 48 may include a plurality of vent holes 52 that are configured to allow for pressurized steam to escape and have a regulating effect on the pressurized steam applied to the eyes of patient 34. In embodiments, patient 34 may be exposed to pressurized steam via the goggle steam applicator 48 in temperature ranging from 90-105 F (32-40 C).

The therapy equipment 10 is capable of delivering pressurized steam, saturated with organic and/or plant compounds at regulated temperatures and in sufficient quantity to dilate the pores of the skin of a patient 34 by inducing perspiration. The perspiration of patient 34 permits the body of patient 34 to rid itself of toxin via the dilated skin pores.

The steam generator 22, including a pot 24 and a compressor 26, heat water and an organic/plant compound mixture and pressurize the resultant steam, respectively. The pressurized steam from steam generator 22 is conducted to the therapy equipment 10 via piping 28 and may include one or more valves 30. The piping 28 may be constructed of heat resistant and/or insulative materials in order to maintain the steam as it is conducted via the piping 28 to the therapy equipment 10. As a result, piping 28 may be resistant to the formation of condensation due to the lower temperature surrounding the piping 28.

The therapy equipment 10 may be of a square or rectangular shape, in order to receive a patient 34 inside. In embodiments, therapy equipment 10 may be constructed in other shapes and/or sizes, such a size sufficient to accommodate more than one patient at a time. The therapy equipment 10 described herein is merely exemplary and not limiting. Patient 34 enters the therapy equipment 10 via a panel 14 that pivots about one or more hinges 18. As illustrated in FIG. 1, for example, the front panel 14 may pivot upward to allow patient 34 to enter the therapy equipment 10. In embodiments, front panel 14 may be configured to pivot to a side via hinges 18. In embodiments, a side, top or bottom panel 14 may also be configured to pivot about one or more other panels 14 via hinges 18, to permit patient 34 to enter the therapy equipment 10. Panels 14 may be supported and/or joined together at least in part by a frame 12. Frame 12, which may be constructed of a suitable strong material (e.g., metal, stainless steel, aluminum, and/or wood, or a combination thereof), may engage one or more panels 14. In embodiments, panels 14 may be joined to each other forming a therapy equipment 10 and placed within frame 12. In embodiments, panels 14 may be joined to elements of frame 12 and together form a therapy equipment 10. In embodiments, frame 12 and panels 14 may be integrated, at least partially.

Therapy equipment 10 may include one or more windows 16. Once a patient 34 enters the therapy equipment 10, the windows 16 allow the patient 34 to communicate with the therapy equipment operator/technician (not shown). Patient 34 may then lie down inside therapy equipment 10, on the bottom panel 14. Bottom panel 14 may include padding and/or cushions to support patient 34 within the therapy equipment 10.

Figure 2:
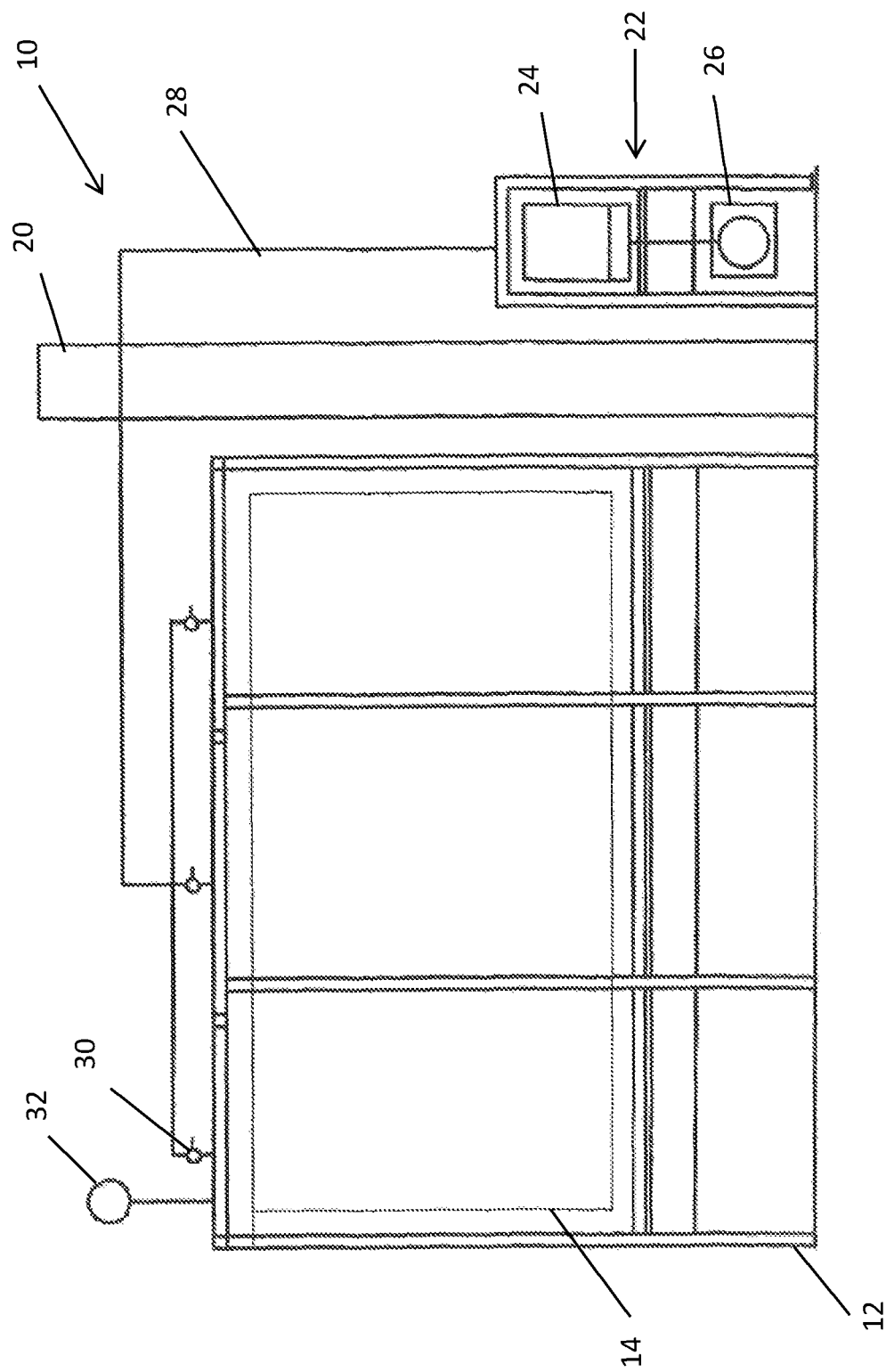
FIG. 2 is a rear view generally illustrating an embodiment of a steam therapy equipment, in accordance with teachings of the present disclosure.
Figure 3:
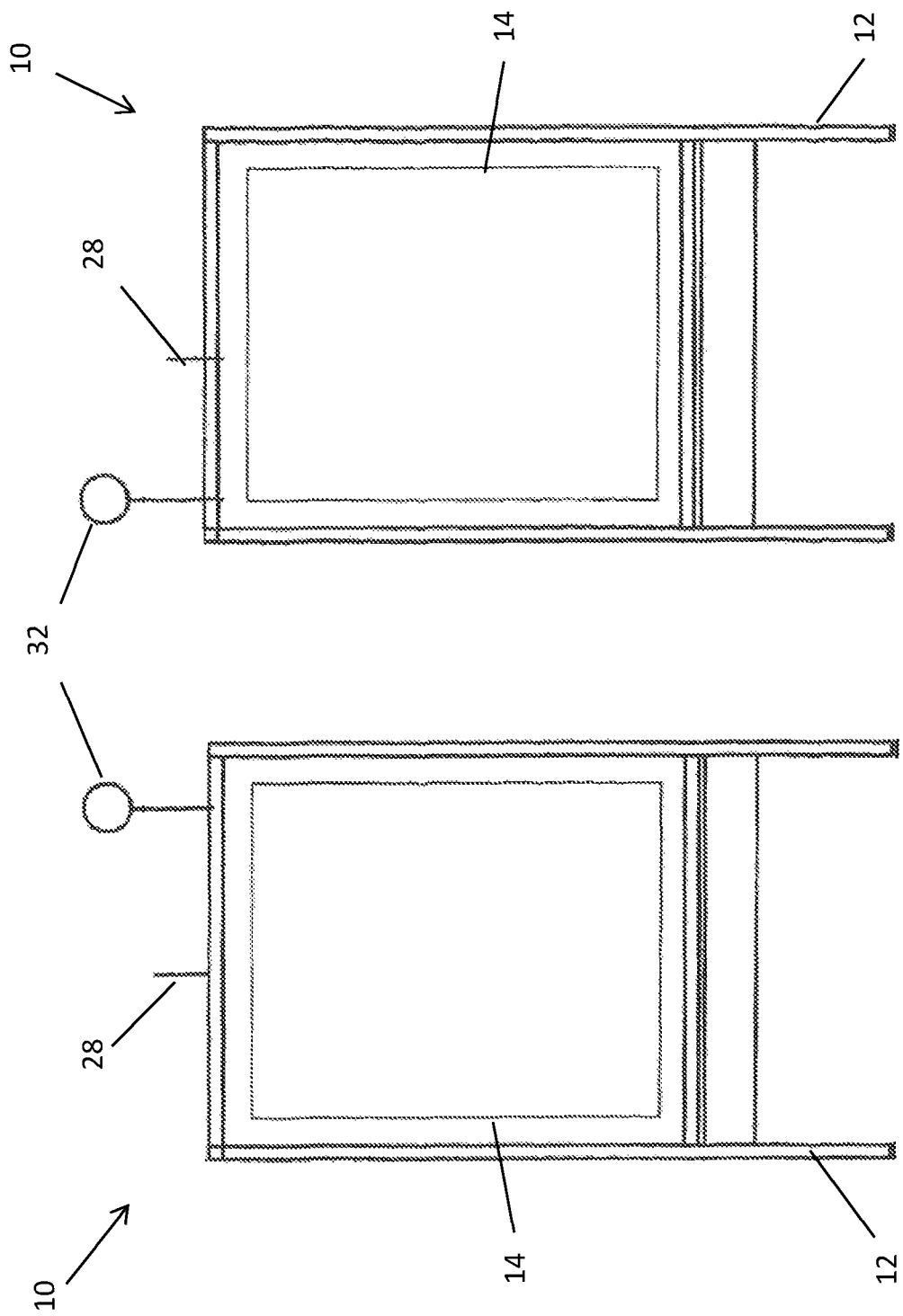
FIG. 3A is a left side view generally illustrating an embodiment of a steam therapy equipment, in accordance with teachings of the present disclosure.
FIG. 3B is a right side view generally illustrating an embodiment of a steam therapy equipment, in accordance with teachings of the present disclosure.

Pressurized steam from the steam generator 22 is conducted via piping 28 into the therapy equipment 10 and is regulated by a plurality of valves 30. The valves 30 may be opened or closed by the operator/technician to regulate the amount of pressurized steam entering the therapy equipment 10 as well as the location of the pressurized steam entering the therapy equipment 10, as illustrated in FIGS. 1, 2 and 5. Temperature sensor 32 displays the current temperature of the pressurized steam within the therapy equipment 10 for the operator/technician to monitor and adjust the operation of steam generator 22 as needed.

Depending upon the type of ailment and the preferred/ideal treatment, a steam generator 22 of a therapy equipment 10 is filled with water and organic/plant material and heated to produce steam, which is then conducted via piping 28 to the interior of therapy equipment 10. Once the temperature within the equipment (i.e., chamber), reaches approximately 115 degrees F. (46 degrees C.), a patient 34 enters the therapy equipment 10 via the hinged panel 14, and lays down inside the therapy equipment 10. The hinged panel 14 is then closed by the operator/technician and the pressurized steam continues to fill the interior of therapy equipment 10.

Patient 34 may be oriented inside therapy equipment 10 such that the head of patient 34 is positioned away from a drain 40 inside therapy equipment 10. As patient 34 is exposed to the pressurized steam in the therapy equipment 10, the patient 34 begins to perspire (i.e., sweat). Additionally, pressurized steam may also condensate into water within the therapy equipment 10, which due to the configuration of the bottom panel 14, causes the liquid water to collect at drain 40, and away from patient 34. In embodiments, a grate or similar device (not shown) may be placed on the interior bottom of the therapy equipment 10, upon which padding (not shown) for support of the patient 34 is installed. The grate may be configured to position the padding above the interior surface of the bottom panel 14 to promote the movement of liquid water within the therapy equipment to the drain 40.

Figure 4:
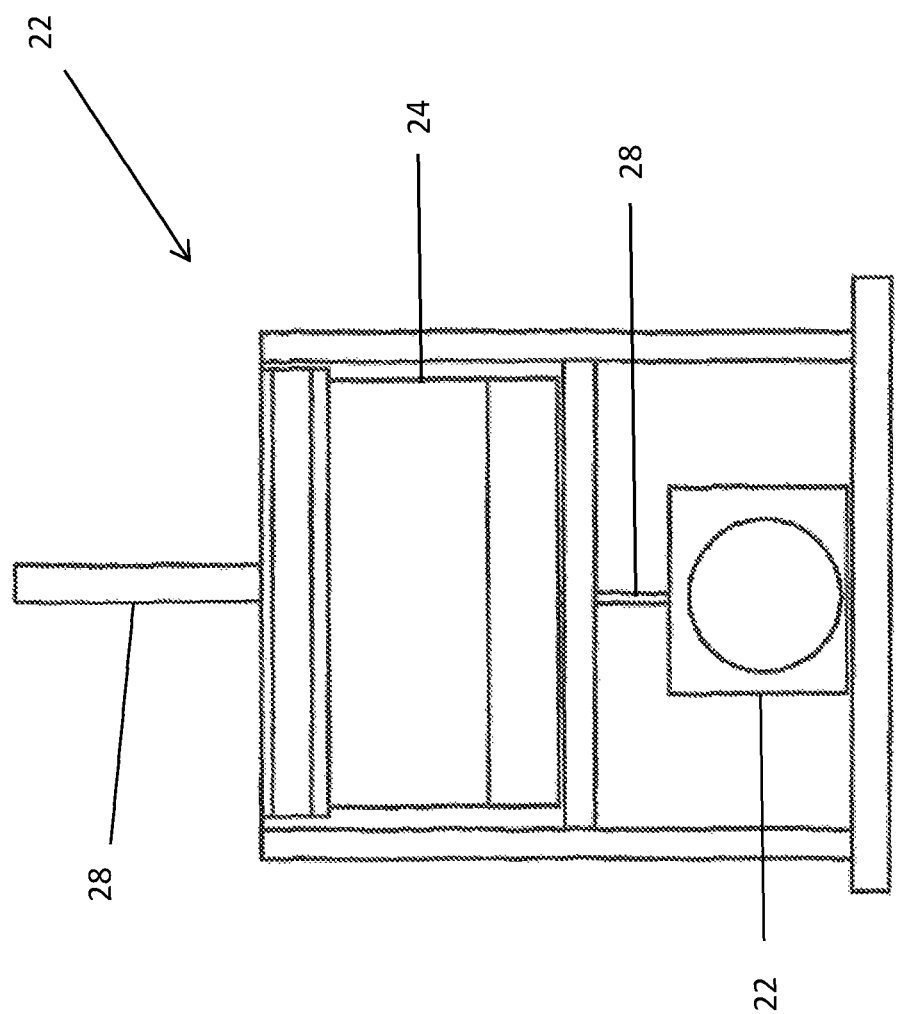
FIG. 4 is a sectional view of embodiments of a steam generator and compressor associated with a steam therapy equipment, in accordance with teachings of the present disclosure.

Referring now to FIG. 4, an embodiment of a steam generator 22 of a therapy equipment 10 is shown. Steam generator 22 includes a pot 24 for mixing and heating water and a plant/organic mixture and a compressor 26. Piping 28 fluidly joins pot 24 and compressor 26 such that compressed air may enter pot 24. In embodiments, pot 24 may include a lid with two holes. Through the first hole piping 28 is connected that leads to therapy equipment 10 and the second hole connects piping 28 to compressor 26. When pot 24 is heated (e.g., a heat source is applied), and compressor 26 forces air into the now heated pot 24, pressurized steam is forced out of pot 24 through piping 28 to the therapy equipment 10.

In embodiments, a therapy equipment 10 according to the present disclosure is operated as follows. A blend of plant and organic materials (e.g., leaves, bark), is heated in a pot 24 with purified water, dissolving the plant and organic materials in the water, which is turned into steam via heating. A compressor 26 pressurizes the steam and piping 28 conducts the pressurized steam to the therapy equipment 10. A patient 34 inside the therapy equipment 10 may be exposed to the pressurized steam for a predetermined time (e.g., 10-45 minutes). It should be understood that other exposure times are contemplated, and the examples provided are not limiting. In embodiments, the patient 34 may be given some of the water and plant/organic heated mixture by the operator/attendant to drink outside of the therapy equipment 10.

In embodiments, pressurized steam from a steam generator 22 of a therapy equipment 10 may be conducted via flexible adapter 56 to one or more applicators 44, 46, and 48 (as shown in FIGS. 6A-6C) to treat areas such as respiratory, eye, ear, nose and/or throat. For treatment using the applicators 44, 46, and 48, a patient 34 may be seated outside the therapy equipment 10 and the applicators 44, 46, and 48 are placed in direct contact with a portion of the body of patient 34 for a predetermined period of time. Patient 34 may receive more than one type of treatment via applicators 44, 46, and 48, such as respiratory, eye, ear, nose, and throat treatment.

In embodiments, a patient 34 may be treated by a therapy equipment 10 three times a week for a period of 15-45 minutes each. More or less treatment frequencies and durations are also contemplated; the embodiments provided are merely exemplary. In embodiments, the whole body of patient 34 may be treated within therapy equipment 10, or portions of the body of patient 34 may be treated, such as the eyes of the patient 34 for refractive errors of the eye, respiratory, ear, nose and throat disorders; the torso/waist and/or joint of the patient 34 for inflammation.

In embodiments, the water and plant/organic mixture may take into consideration the health condition and/or physical state of a patient 34. For example, the following items may be used to treat the following afflictions:

| | |
|---|---|
| a) Neem leaves (6 parts by weight). | For treating afflictions including but not limited to: malaria, dengue fevers, and detoxification. |
| b) Pawpaw leaves (4 parts by weight). | |
| c) Guava leaves (4 parts by weight). | |
| d) Orange leaves (4 parts by weight). | |
| Soursop leaves (4 parts by weight). | |
| Black walnut bark (2 parts by weight) | |
| a) Horse radish leaves (6 parts by weight). | Used as a detoxifying agent/diuretic in cases of edema and for treatment of inflammation. |
| b) Avocado leaves (2 parts by weight). | |
| c) Cherry leaves (1.5 parts by weight). | |
| d) Guava leaves (5 parts by weight). | |
| e) Turmeric root (2 parts by weight). | |
| a) Licorice root (1 part by weight). | For treatment of refractive errors of the eyes. |
| b) Lemon peel (1 part by weight). | |
| c) Almond leaves (1 part by weight). | |
| d) Chicory (1 part by weight). | |
| e) Carrot (2 parts by weight). | |
| f) Spinach leaves (1 part by weight). | |
| g) Coconut (0.5 parts by weight). | |
| h) Bilberry (1 part by weight). | |
| i) Indian gooseberry (1 part by weight). | |
| a) Apple leaves (4 parts by weight). | For treatment of hypertension and/or vascular problems. |
| b) Mango leaves (2.5 parts by weight). | |
| c) Beets root (4 parts by weight). | |
| d) Spinach leaves (4 parts by weight). | |
| e) Carrot (2 parts by weight). | |

The above mixtures and formulations of plants and organic matter are used to ensure that the treatment of the therapy equipment 10 is effective. The specific treatment process described herein is developed and tested to enhance the ancient "Igbo" art of "Ogwu Okpukpu", a naturopathic treatment for different forms of toxin-induced ailments and/or afflictions and the complications they bring about.

Although only certain embodiments have been described above with a certain degree of particularity, those skilled in the art could make numerous alterations to the disclosed embodiments without departing from the scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments. Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While one or more particular embodiments have been shown and described, it will be understood by those of skill in the art that various changes and modifications can be made without departing from the spirit and scope of the present teachings.

What is claimed is:

1. A method for applying steam to a human body comprising:
    placing at least one organic plant part in a vessel;
    adding water to the vessel;
    mixing the at least one organic plant part with the water to form a mixture;
    heating the mixture to produce steam;
    forcing air into the vessel via a compressor to pressurize the steam;
    piping the pressurized steam into a steam therapy equipment, wherein the steam therapy equipment comprises at least one steam applicator; and
    exposing the human to the pressurized steam via the at least one steam applicator.

2. The method of claim 1, further comprising:
    attaching the at least one steam applicator to the steam therapy equipment via a flexible adapter to reduce the pressurized steam;
    placing the at least one steam applicator in contact with a portion of the body of the human; and
    concentrating the pressurized steam on the portion of the body via the at least one steam applicator for a predetermined period of time.

3. The method of claim 1, further comprising providing the human with the mixture to be drunk by the human.

4. The method of claim 1, further comprising: attaching the at least one steam applicator to the steam therapy equipment via a flexible adapter to reduce or receive the pressurized steam;
    placing the at least one steam applicator in contact with a first portion of the body of the human; and
    concentrating the pressurized steam on the first portion of the body of the human via the steam applicator for a first predetermined period of time.

5. The method of claim 4, further comprising:
    removing the at least one steam applicator from the first portion of the body of the human for a second predetermined period;
    placing the at least one steam applicator in contact with the first portion of the body of the human; and
    concentrating the pressurized steam on the first portion of the body of the human via the steam applicator for a third predetermined period of time.

6. The method of claim 4, further comprising:
    removing the at least one steam applicator from the first portion of the body of the human for a fourth predetermined period;
    placing the at least one steam applicator in contact with a second portion of the body of the human; and
    concentrating the pressurized steam on the second portion of the body of the human via the steam applicator for a fifth predetermined period of time.

7. The method of claim 1, wherein the at least one organic plant part is selected from the group consisting of:
    a) neem leaves;
    b) pawpaw leaves;
    c) guava leaves;
    d) orange leaves;
    e) soursop leaves; and
    f) black walnut bark.

8. The method of claim 1, wherein the at least one organic plant part is selected from the group consisting of:
    a) horse radish leaves;
    b) avocado leaves;
    c) cherry leaves;
    d) guava leaves; and
    e) turmeric root.

9. The method of claim 1, wherein the at least one organic plant part is selected from the group consisting of:
    a) licorice root;
    b) lemon peel;
    c) almond leaves;
    d) chicory;
    e) carrot;
    f) spinach leaves;
    g) coconut;
    h) bilberry; and
    i) Indian gooseberry.

10. The method of claim 1, wherein the at least one organic plant part is selected from the group consisting of:
    a) apple leaves;
    b) mango leaves;
    c) beet root;
    d) spinach leaves; and
    e) carrot.

11. The method of claim 2, further comprising sealingly engaging the at least one steam applicator against the portion of the body of the human.

12. The method of claim 11, further comprising:
   causing the pores of the skin of the human to dilate via the pressurized steam; and
   causing the pressurized steam to be absorbed into the skin or bloodstream of the human.

13. The method of claim 11, further comprising exposing the human to the pressurized steam at a predetermined temperature.

14. The method of claim 11, further comprising sealingly engaging the at least one steam applicator against an eye of the human, wherein the eye of the human is completely disposed within the seal created by the at least one steam applicator.

15. The method of claim 14, further comprising exposing the human to the pressurized steam at a predetermined temperature.

16. The method of claim 11, further comprising sealingly engaging the at least one steam applicator against a mouth and a nose of the human, wherein the mouth and the nose of the human are completely disposed within the seal created by the at least one steam applicator.

17. The method of claim 16, further comprising exposing the human to the pressurized steam at a predetermined temperature.

18. The method of claim 17, further comprising the human inhaling the pressurized steam.

19. The method of claim 11, further comprising sealingly engaging the at least one steam applicator against an ear of the human, wherein the ear of the human is completely disposed within the seal created by the at least one steam applicator.

20. The method of claim 19, further comprising exposing the human to the pressurized steam at a predetermined temperature.

* * * * *